United States Patent
Weiner et al.

(10) Patent No.: US 8,775,203 B2
(45) Date of Patent: Jul. 8, 2014

(54) ICE DIET SYSTEM AND METHODS OF IMPLEMENTING SAME

(76) Inventors: Brian C. Weiner, Morganville, NJ (US); Alex C. Weiner, Morganville, NJ (US)

( * ) Notice: Subject to any disclaimer, the term of this patent is extended or adjusted under 35 U.S.C. 154(b) by 345 days.

(21) Appl. No.: 13/105,929

(22) Filed: May 12, 2011

(65) Prior Publication Data

US 2011/0282810 A1    Nov. 17, 2011

Related U.S. Application Data

(60) Provisional application No. 61/345,094, filed on May 15, 2010.

(51) Int. Cl.
*G06Q 50/00* (2012.01)
*G01G 19/414* (2006.01)
*G06F 19/00* (2011.01)

(52) U.S. Cl.
CPC ........ *G01G 19/4146* (2013.01); *G06F 19/3475* (2013.01); *G06F 19/3487* (2013.01)
USPC ........................................... 705/2; 177/25.16

(58) Field of Classification Search
USPC .......................................................... 705/2–3
See application file for complete search history.

(56) References Cited

U.S. PATENT DOCUMENTS

| | | | |
|---|---|---|---|
| 6,856,938 B2 * | 2/2005 | Kurtz | 702/173 |
| 2003/0187683 A1 * | 10/2003 | Kirchhoff et al. | 705/1 |

OTHER PUBLICATIONS

"The Ice Diet"; The last word; Author: Anonymous; Publication info: New Scientist 188. 2530 (Dec. 17-Dec. 23, 2005): 0_3.*

* cited by examiner

*Primary Examiner* — Minnah Seoh
(74) *Attorney, Agent, or Firm* — Jon Fallon, Esq.; Michael P. Kochka, Esq.

(57) ABSTRACT

Embodiments of the present invention relate to system and method of dieting, wherein safe increases to an individual's basal metabolic rate accelerates the burning of fat, and may be used as a primary method of weight loss and/or as a complementary technique to the success of other weight loss strategies. In one embodiment of the present invention, a method of weight loss comprises measuring a temperature and quantity of a consumable product; determining a gross caloric value of the consumable product; calculating an energy to be expended during consumption of the consumable product by an individual; calculating a net caloric value of the consumable product, wherein the net caloric value is equal to a gross caloric value of the consumable product less the caloric energy expended by an individual in consuming the consumable product; and tracking the net caloric value over a predetermined time interval.

6 Claims, 2 Drawing Sheets

ICE DIET SYSTEM AND METHODS OF IMPLEMENTING SAME

CROSS-REFERENCE TO RELATED APPLICATIONS

This application claims priority to U.S. Provisional Patent Application Ser. No. 61/345,094, filed May 15, 2010, entitled "The ice diet, a novel method for weight loss and a method for enforcing the licensing of the diet," the disclosure of which is incorporated herein by reference in its entirety.

BACKGROUND

1. Field of the Invention

Embodiments of the present invention are generally to an ice diet system and methods of implementing same. More specifically, embodiments of the present invention relate to system and method of dieting, wherein safe increases to an individual's basal metabolic rate accelerates the burning of fat, and may be used as a primary method of weight loss and/or as a complementary technique to the success of other weight loss strategies.

2. Description of the Related Art

Human obesity is a major medical and social problem. It is well known that a large percentage of the population is obese, overweight, or is prone to being overweight, and constantly trying to lose weight. Obesity may generally be defined as a condition of excess body fat, which serves as a store house of energy. Energy from fat and ingested foods is used to power of the body's metabolic needs. For example, an active teenage male is estimated to burn 3067 calories per day for needed energy.

There are four primary known methods of treating obesity, namely (1) dietary manipulation (i.e., dieting), (2) exercise, (3) medication, and (4) surgical treatments. Unfortunately, all currently known methods of treatment of obesity, whether alone or in combination, have limited effectiveness and significant adverse side effects, and each technique has pitfalls which limits their applicability and effectiveness.

Dietary manipulations (i.e., diets) are meant to limit or decrease the number of ingested calories of food per day, to create a calorie or energy deficit. Such calorie deficit would generally cause the body to draw energy off of its stores of fat. However, for many obese people, traditional dieting yields a feeling of starvation, and as such, compliance with the diet becomes difficult.

During exercise, energy is burned to perform the work associated with the exercise. The energy required for the exercise would generally lead to drawing energy off from the stores of fat. However, obese patients typically have difficulty in complying with exercise programs due to physical limitations and pain, both of which often result from the patient's obesity in the first place.

Available medications have limited effectiveness and may have undesirable side effects. These drugs are intended to decrease the appetite for food, or interfere with the absorption of food energy in the gastrointestinal tract. As such, they have marginal effectiveness treating obesity. Similarly, surgical procedures are invasive and subject to complication, and as such are not often utilized as an effective means to lose weight.

In practice, physicians generally recommend combinations of these strategies for their patients. However, even in combination, the strategies are less effective than patients or their physicians would like. As such, there is a need for an improved system and method for treating obesity.

SUMMARY

Embodiments of the present invention are generally to an ice diet system and methods of implementing same. More specifically, embodiments of the present invention relate to system and method of dieting, wherein safe increases to an individual's basal metabolic rate accelerates the burning of fat, and may be used as a primary method of weight loss and/or as a complementary technique to the success of other weight loss strategies.

In one embodiment of the present invention, a method of weight loss comprises: measuring a temperature and quantity of a consumable product; determining a gross caloric value of the consumable product; calculating an energy to be expended during consumption of the consumable product by an individual; calculating a net caloric value of the consumable product, wherein the net caloric value is equal to a gross caloric value of the consumable product less the caloric energy expended by an individual in consuming the consumable product; and tracking the net caloric value over a predetermined time interval.

In another embodiment of the present invention, a method of weight loss comprises: measuring the temperature and quantity of a frozen consumable product; determining a gross caloric value of the consumable product; adding a first energy, a second energy, and a third energy together to yield a total energy expended during consumption of the consumable product by the individual, wherein: the first energy is calculated by multiplying a frozen specific heat value of the frozen consumable product by the quantity and by a net temperature difference between the temperature and the freezing point of the frozen consumable product; the second energy is calculated by multiplying a latent heat of fusion of the frozen consumable product by the quantity; and the third energy is calculated by multiplying the non-frozen specific heat value of the frozen consumable product by the quantity and by a net temperature difference between a body temperature of the individual and the freezing point of the consumable product; calculating a net caloric value of the frozen consumable product, wherein the net caloric value is equal to the gross caloric value of the frozen consumable product less the caloric energy expended by an individual in consuming the frozen consumable product; and tracking the net caloric value over a predetermined time interval.

In yet another embodiment of the present invention, a consumable product advertisement comprises a description of the consumable product; and a net caloric value of the consumable product, wherein the net caloric value is equal to a gross caloric value of the consumable product less the caloric energy expended by an individual in consuming the consumable product.

BRIEF DESCRIPTION OF THE DRAWINGS

So the manner in which the above-recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments of embodiments encompassed within the scope of the present invention, and, therefore, are not to be considered limiting, for the present invention may admit to other equally effective embodiments, wherein.

Figure 1:
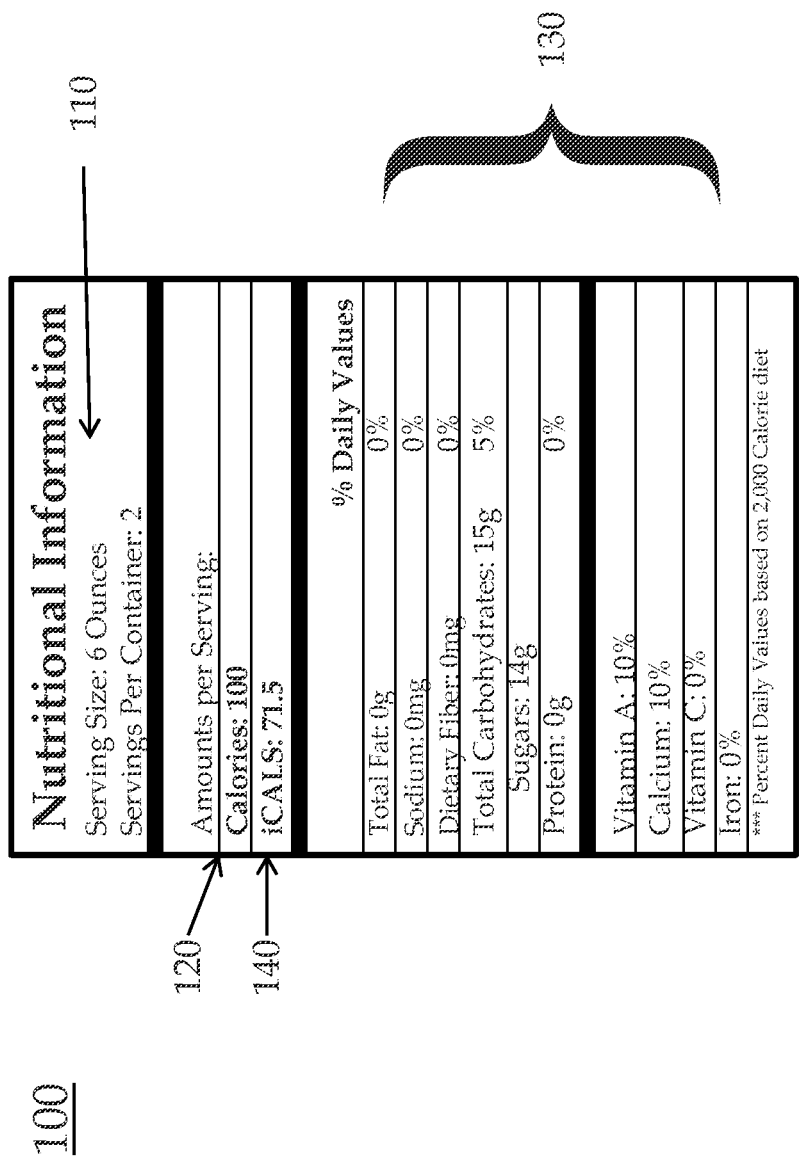
FIG. 1 depicts an exemplary nutritional label for food products in accordance with embodiments of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present invention are generally to an ice diet system and methods of implementing same. More specifically, embodiments of the present invention relate to system and method of dieting, wherein safe increases to an individual's basal metabolic rate accelerates the burning of fat, and may be used as a primary method of weight loss and/or as a complementary technique to the success of other weight loss strategies.

Humans are homeotherms, meaning they regulate their body temperature fairly effectively within a rather small range of temperatures. It has been estimated that over 60% of the body's energy use is for involuntary purposes, such as basic metabolism or functions of internal organs, and the energy burned for these involuntary purposes is not under conscious or voluntary control. It is the heat energy given off by these basic metabolic processes that is used to maintain healthy patients at a stable body temperature, i.e., approximately 37° C.

Pure water, i.e., $H_2O$, generally has no calories that can be utilized or burned for basic metabolism; however, it does have energy inherently stored therein. In the average home freezer, the temperature is around −20° C. (i.e., about −4° F.). Under those conditions, water would generally freeze into a solid form, i.e., "ice."

If an individual were to ingest ice at −20° C., it would first have to be warmed from −20° C. to about 0° C., which requires energy. At 0° C., the ice will melt into liquid water, which is an endothermic reaction, requiring additional energy. Then, due to the individual's need to maintain a stable core temperature, the 0° C. water must generally be warmed to about 37° C., which again requires energy.

When dealing with nutrition, it is common to utilize the unit of Calorie (or kilocalorie) when discussing the energy present within the consumable product. A Calorie is defined as the energy needed to increase the temperature of 1 kilogram of water by 1° C. For purposes of simplicity in explanation, 1 kg of water is approximately 1 Liter of water (i.e., assuming standard atmospheric pressure, and environmental temperatures between about −30° C. and about 40° C.). As such, for purposes of embodiments of the present invention, it takes one Calorie of energy to warm one Liter of water by one 1° C. In addition, it is known that in order to convert solid ice to liquid water, which occurs exactly at 0° C., requires approximately 79.72 Calories of energy per kilogram of water (i.e., the latent heat of fusion of water is about 80 Calories/kg).

As such, in one embodiment of the present invention, if a patient were to ingest 1 L of ice at −20° C., that patient would burn approximately 20 Calories warming the ice to 0° C., approximately 80 Calories converting the solid ice into liquid water, and approximately 37 additional Calories heating the liquid water from 0° C. to about 37° C. As such, according to basic thermodynamic calculations, the patient would burn about 137 Calories when consuming 1 Liter of ice at −20° C. Please note, in practical embodiments, additional energy would be expended assuming the patient chewed the ice, swallowed it, etc. However, for purposes of embodiments of the present invention, the discussion will be limited to the monitoring and analysis of the latent energy expenditure and not the parameters that vary greatly from patient to patient.

In many practical embodiments, it is noted that a patient's metabolism is not completely efficient, and often wastes additional energy during certain processes. Thus, an individual would utilize greater than approximately 140 Calories of energy by consuming 1 L of ice. As the human metabolic inefficiency has been estimated to be between about 10 and 20%, a patient would likely utilize between about 154 to 168 Calories of energy when consuming 1 L of ice. As such, for exemplary purposes only, 160 Calories/Liter is the approximation utilized herein for exemplary embodiments of the present invention. It should be appreciated however, variations up to about 30% (i.e., from about 112 Calories/Liter up to about 208 Calories/Liter) should be deemed reasonably within an acceptable range for embodiments of the present invention.

In one embodiment, for example, the case of the healthy 18-year-old male teenager who consumes approximately 3067 Calories per day, a 160 calorie deficit represents approximately 5% of the patient's daily intake. In another exemplary embodiment, however, involving an older patient consuming only about 2000 Calories per day, a 160 Calorie deficit represents about 8% of the patient's daily intake.

In accordance with embodiments of the present invention, an individual's expenditure of about 160 Calories by the above method is similar to the amount of energy expended by a 200 pound person running one 6 minute mile (i.e., at 10 miles per hour). Similarly, since it is known that one pound of body fat requires approximately 3500 Calories of energy to burn, an individual's expenditure of about 160 Calories by the above method is similar to burning ¾ of one ounce of body fat. Stated in other terms, if an individual were to consume 1 L of ice per day for a 30 day period, about 4800 Calories would be burned, which represents about 1.37 pounds of body fat.

While the above discussion pertains to pure water, there are a variety of foods, beverages, or similar consumable products that may be consumed in a frozen state. In fact, certain foods are meant to be eaten in a frozen state. For example, for one brand of frozen confectionary ices, a 6 ounce portion (i.e., 0.178 L) comprises approximately 100 Calories as listed on the nutritional information chart on the product. Generally, most nutritional caloric measurements are conducted by assessing the known calorie contents of the various components that make up the product, and adding them together.

However, in accordance with embodiments of the present invention, the actual number of calories the patient realizes from consuming such product would be less than the calories noted on the nutritional information on the product packaging. That is, the net calories consumed by the patient comprises the energy inherent in the consumable product (i.e., the calories noted on the nutritional information) less the amount of energy that the patient would utilize to digest and warm the product to body temperature.

In the example above, wherein an individual consumes a 6 ounce (0.178 L) portion of frozen confectionary ice, the energy required to warm the product to body temperature could be calculated, assuming all 0.178 L of product comprises the same specific heat as water (i.e., 1 Calorie/kg). Using the approximation that 160 Calories are utilized by an individual when consuming 1 L of ice, it can be calculated that consuming the frozen confectionary ice would require approximately 28.5 Calories of energy (i.e., 0.178 L×160 Cal/liter of ice). Thus, in accordance with embodiments of the present invention net caloric intake would be approx. 71.5 Calories (i.e., 100 Calories (as listed on the nutritional information label) less 28.5 Calories burned during consumption).

In many embodiments, the manufacturer of the consumable product would likely want to advertise of this advantageous correction of nutritional information to consumers. FIG. 1 depicts an exemplary nutritional label for food products in accordance with embodiments of the present invention. In one embodiment, the nutritional label 100 generally comprises a recommended serving size and portion 110, the latent gross calories of the product 120, the general nutritional information 130, and the net caloric value of the product 140. In accordance with embodiments of the present invention, the "net caloric value" or "net calories" of a consumable frozen product may generally be called "ice calories", or as shown in the Figure, "iCALS."

As understood by embodiments of the present invention, a nutritional label 100 may generally be provided on the surface of product packaging, on advertisements, or the like. In some embodiments, it may be advantageous to a product packaging having the designation for the net calories 140 listed elsewhere on the product (e.g., across the front of the package) or product advertisement. As such, a consumer may be drawn into purchasing a particular product because of its net caloric value, and placement of such net caloric value may be commercially valuable to a manufacturer or distributor of such products.

In another embodiment, if a frozen confectionary ice was artificially flavored, and had zero or few calories by standard calculation, simple ingestion of the product may actually lead to a negative caloric intake, or weight loss. For example, if the 6 ounce frozen confectionary ice described above only comprised 20 Calories by standard measurement, the net caloric intake of the frozen confectionary ice may be a negative 8.5 Calories—that is, a dessert with a fat burning effect.

Many embodiments of the present invention may be suitable for products that are kept and/or ingested above freezing temperatures. In fact, any food or consumable product ingested at a temperature below about 37° C. would have a net caloric value less than the traditional gross calorie value of the product. However, as there is no effect of the energy of enthalpy of melting ice in the digestion of these foods, the magnitude of calorie burning effects of these foods are necessarily smaller than in the case of frozen foods. In accordance with embodiments of the present invention, to calculate the net caloric value of such products an individual would need to measure the serving temperature, the weight and the heat content of the portion of food. In one example where an individual drinks 1 L of water at 20° C., the calculation to determine the energy expended to heat the consumed water to body temperature would be the temperature difference (i.e., 17° C.) multiplied by the quantity in Liters (i.e., 1 Liter), yielding 17 Calories expended. While this is significantly less than the approximately 160 Calories used to consume 1 L of ice, energy is still burned.

Embodiments of the present invention may also be suitable for foods typically served at a temperature greater than 37° C. In such embodiments, an individual's body must expend energy to cool the food to body temperature, and the same process described above can be utilized here as well (i.e., a net temperature differential between ingested food and core body temperature is all that is required). However, to distinguish the net caloric value from cooling ingested food from the "ice calories" described above, the term "fire and ice calories," "fire calories," or simply "fiCALS," may be utilized. In many embodiments, manufacturers of food products and others involved in the retail distribution of foods, e.g., restaurateurs, may wish to emphasize the net caloric value, "iCALS" or "fiCALS," of a product or meal to enhance its desirability.

Although water is primarily discussed above, embodiments of the present invention extend to other consumable products as well. In order to calculate the iCALS or fiCALS of the specific consumable product, the specific heat of the consumable product needs to be determined. Generally, the specific heat of most known food products is publicly available (e.g., as tracked and cataloged by the United States Department of Agriculture). For example, an apple at room temperature (i.e., 20° C.) has a specific heat of about 0.87 Calories/(kg·° C.), and is about 0.154 kg in size. Thus, the energy expended to bring a consumed apple to body temperature (i.e., 37° C.) is the specific heat, multiplied by the mass, multiplied by the change in temperature:

$$0.87 \text{ Calories}/(\text{kg}\cdot°\text{C.})\times 0.154 \text{ kg}\times 17°\text{ C.}=2.28 \text{ Calories}.$$

Thus, while an apple may be generally listed as having about 80 Calories on a nutritional label, the iCals for an apple at room temperature are about 77.7.

Similar to the above example, certain frozen products may contain osmotically active solutes, which alter the specific heat of the product. Generally, the heat required to melt such frozen products and raise it to body temperature may be greater than in the example of frozen water or ice. As such, for certain frozen products, modifications may be made to calculations by acquiring the specific heat of the frozen products at freezing temperatures, specific heat of the frozen products at non-freezing temperatures, and the latent heat of fusion (i.e., energy) required to melt the frozen product. In one embodiment, to calculate the energy expended during consumption, the following equation may be utilized:

$$\text{Energy}=[(\text{specific heat frozen})\times(\text{mass})\times(\text{freezing point}-\text{frozen temperature})]+[(\text{latent heat of fusion})\times(\text{mass})]+[(\text{specific heat non-frozen})\times(\text{mass})\times(\text{body temperature}-\text{freezing point})].$$

It should be noted, for purposes of embodiments of the present invention, the values utilized in all calculations should be in their absolute value (i.e., no negative numbers should be multiplied.)

In many embodiments of the present invention, patients may be encouraged to utilize other known mechanisms and methods associated with weight loss, in addition to the "Ice Diet" described herein. Whereas the methodology of embodiments of the present invention would not interfere with any common diet, exercise, drug-prescription or surgical procedure (i.e., ingestion of water is commonly encouraged during all such weight loss methods), it can only benefit individuals seeking to lose weight quickly and safely.

Figure 2:
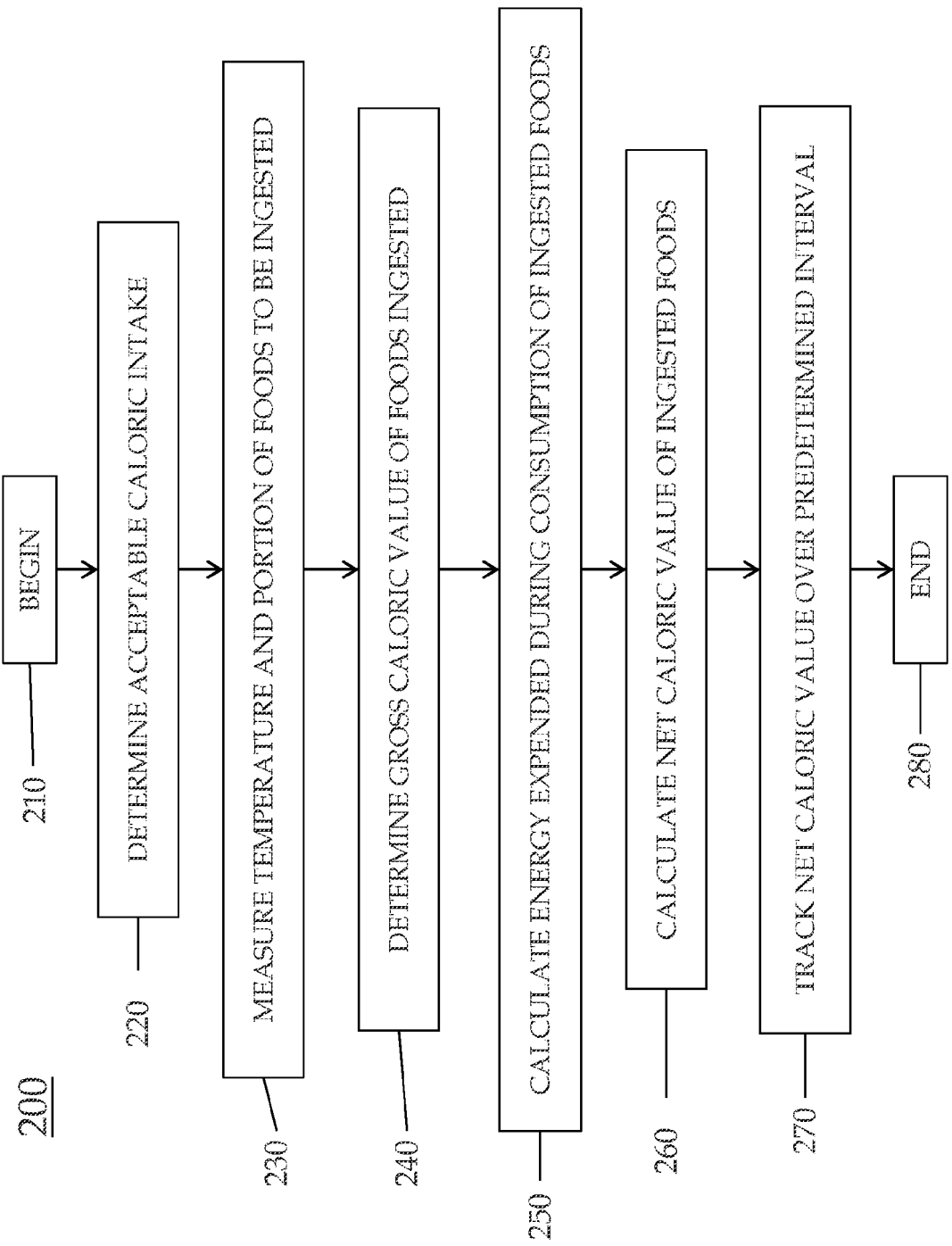
FIG. 2 depicts a flowchart of a method for treating obesity in accordance with one embodiment of the present invention.

Although the methodology of embodiments of the present invention may take numerous forms, FIG. 2 depicts a flowchart of an exemplary method in accordance with one embodiment of the present invention. The method 200 begins at step 210.

At step 220, a patient determines an acceptable caloric intake over a predetermined period of time. For example, in one embodiment, a patient may be told by her doctor that she should limit her daily calorie intake to 2000 Calories. In other embodiments, an individual may obtain a recommended daily calorie intake from the United States Department of Agriculture (e.g., according to the USDA's recommended food plan, a 30 year old male, who is 5' 11" tall, and weighs 230 pounds should consume about 2600 Calories per day). In further embodiments, an acceptable caloric intake over a period of time may be determined by the patient, either arbitrarily, through past behavior, or the like. In accordance with embodiments of the present invention, this step 220 may only be necessary where the patient has a preconceived notion of intended weight loss. In certain alternative embodiments, the "ice diet" methodology presented herein, may be followed unintentionally, in which case it may be unlikely the patient has determined an acceptable caloric intake over a predetermined period of time.

At step 230, the temperature and portion size (i.e., mass) of foods or other consumable products to be ingested are measured. In one embodiment, the temperature may be measured using a standard food-grade thermometer, and the portion size may be weighed to obtain an accurate value. However, in certain embodiments, the temperature of the food may be guessed, for example, by using a base-line judgment. In one example, if a food is frozen (e.g., ice cream), it can be presumed to be somewhere between a complete solid (i.e., at $-20°$ C.) and a liquid (i.e., at $0°$ C.), which may be guessed around $-10°$ C. In other embodiments, the portion size may be estimated from advertised or listed amounts. For example, a 12 ounce steak on a restaurant menu (which is usually the pre-cooked weight), may weigh about 10.8 ounces (about 10% less) when consumed.

At step 240, the gross caloric value of the foods ingested may be determined. In one embodiment, the determination may be made by reviewing a nutritional label or other listed source regarding the calories of the food (e.g., a restaurant menu, a website, a food guide, or the like). In alternative embodiments, the gross caloric value of the food may be determined using a calorimeter. In another embodiment of the present invention, the gross caloric value of the food may be estimated by comparison to other similar foods for which such data is known.

At step 250, the energy expenditure for consuming the foods at the temperature and portion size measured may be calculated. As disclosed herein, by knowing the specific heat, temperature and mass of a food, the energy expended to bring the temperature of the food to the core body temperature of the patient can be calculated. For example, for frozen water-based products, the energy required to consume such products can be calculated by multiplying the volume of product in liters by 160 Calories/Liter. Similarly, for hot water-based products (e.g., hot tea at $80°$ C.), the energy required to consume such products can be calculated by multiplying the volume of product in liters by the temperature differential (i.e., $80°$ C.$-37°$ C.$=43°$ C.). In another example, for non-water based products (e.g., solid foods), the energy required to consume such products can be calculated by multiplying the specific heat of the product by the mass of the product in kilograms, and then multiplying that by the temperature differential in degrees Celsius.

At step 260, once the gross caloric value of the food and the energy expended during consumption of the food are known, the net caloric value of the ingested foods can be calculated. By subtracting the energy expended during consumption of the food from the gross calories extant in the food, the net calories ingested or realized by the patient become apparent. In many embodiments of the present invention, the weight loss methodology disclosed herein is centered around such net caloric value—i.e., through accurately tracking such values and/or by altering a diet routine by consuming foods having lower net caloric value, regardless of their gross calories.

At step 270, the patient may track the net caloric value of consumed foods over a predetermined interval. For example, in one embodiment, a patient may be prescribed a diet in accordance with embodiments of the present invention by a doctor. In such example, the doctor may require the patient to track net caloric values over the course of a week, month, quarter or year, such that the doctor may review such records at a subsequent appointment. In many embodiments, the tracking of the net caloric value may take place in the form of a paper or electronic food or diet journal. Generally, the tracking of the net caloric value of a consumed product is beneficial when comparing it to the acceptable caloric intake set at step 220.

At step 280, the method ends.

With the growing number of Internet-based diet websites, embodiments of the present invention may be easily implemented through a computer-based system, accessible to a variety of users (e.g., patients), via a global-computer network. For example, in accordance with a network-accessible computer system designed for weight-loss may be designed similar to the one disclosed by U.S. Pat. No. 7,523,040, entitled "Software and Hardware System for Enabling Weight Control," assigned to Weightwatchers.com, Inc., the disclosure of which is incorporated herein by reference in its entirety. Although the methodology for weight loss disclosed by such reference is entirely different than embodiments of the present invention, the computer system infrastructure and operational components are explained in such reference as they may exist in an embodiment of the present invention.

In an embodiment utilizing a network-accessible computer-based system, a user may have an account stored within a database on a server within the system, wherein the calculations, computations, tracking, recording and other data-related steps may be accomplished by via computer software stored within the system. For example, in one embodiment, a user may be able to track all net caloric values within an account in the system. In another embodiment, a user may have access to an extensive listing of predetermined net caloric values based upon food selection and quantity. In such an embodiment, the user may only need to select the type of food consumed, and enter the temperature and amount of the portion of the food, and the net caloric value may be calculated automatically. Similarly, by providing such an interactive system, a user may quickly be able to compare the net caloric value of different foods to determine which may be best suited for their dietary needs.

In addition to operating in a computer-network environment, the methodology of embodiments of the present invention may incorporate numerous social-networking functions within the system, to enhance a user's experience therewith. For example, common features of known online communities" may be provided, such as, chat rooms, on-line forums, web logs ("blogs"), etc., so that users of the system may be able to share and/or gather information from other users, medical professionals, third party vendors, or the like.

In other embodiments, to help seek out a party utilizing embodiments of the present invention without permission, the system may comprise a method for the general public to report violators. For example, in one embodiment wherein a computer network infrastructure is utilized, a member of the general public would be encouraged to report any locations where the "Ice Diet" was being offered to potential clients. In such an example, persons providing any such information may be entered into a periodic contest for prizes or other consideration (e.g., a percentage of any subsequently obtained royalties or damages).

In alternative embodiments of the present invention, other strategies could be developed to cool the body, enhancing the burning of fat and increasing the basal metabolic rate. For example, in one embodiment, ice packs could be built into pockets of specially-designed clothing. The clothing may be insulated, particularly the portion of the clothing away from the patient, to prevent or minimize the effect of external energy on the ice packs. As such, the patient's heat energy may be utilized to melt the ice.

In another alternative embodiment, a patients man spray themselves with mixtures of water and/or other evaporating fluids. In such an embodiment, the evaporating and cooling of the liquids would require the expenditure of energy from the patient's body, generally obtained through the burning of fat.

While the foregoing is directed to embodiments of the present invention, other and further embodiments of the invention may be devised without departing from the basic scope thereof. It is also understood that various embodiments described herein may be utilized in combination with any other embodiment described, without departing from the scope contained herein. In addition, embodiments of the present invention may be further scalable, as particular applications may require.

What is claimed is:

1. A computer-implemented method of weight loss comprising:
   receiving, at the computer, a water content of a quantity of a frozen consumable product and a measured quantity of the frozen consumable product;
   accessing, by the computer, a stored gross caloric value of a predetermined quantity of the frozen consumable product;
   determining, by the computer, a gross caloric value of the frozen consumable product based on the stored gross caloric value and the measured quantity of the frozen consumable product;
   calculating, by the computer, caloric energy to be expended during consumption of the frozen consumable product by an individual, the calculating comprising:
      determining a quantity of ice present in the frozen consumable product based on the water content of the frozen consumable product;
      determining the caloric energy required to transform the quantity of ice from a solid state to a liquid state;
   calculating, by the computer, a net caloric value of the consumable product, wherein the net caloric value is equal to a gross caloric value of the consumable product less the caloric energy expended by an individual in consuming the consumable product;
   displaying, by the computer in a coherent display, the gross caloric value of the consumable product and the net caloric value of the consumable product; and
   tracking, by the computer, both the gross caloric value and the net caloric value of consumable products consumed by the individual over a predetermined time interval.

2. The method of claim 1, wherein the consumable product comprises water.

3. The method of claim 1, further comprising:
   comparing, by the computer, the net caloric value over the predetermined time interval to a desired caloric intake over the predetermined interval.

4. A computer-implemented method of weight loss comprising:
   receiving, at the computer a measured quantity of a frozen consumable product and a measured quantity of the frozen consumable product;
   accessing, by the computer, a stored gross caloric value of a predetermined quantity of the frozen consumable product;
   determining, by the computer, a gross caloric value of the frozen consumable product based on the stored gross caloric value and the measured quantity of the frozen consumable product;
   adding, by the computer, a first energy, a second energy, and a third energy together to yield a total energy expended during consumption of the frozen consumable product by the individual, wherein:
      the first energy is calculated by multiplying, by the computer, a frozen specific heat value of the frozen consumable product by the quantity and by a net temperature difference between the temperature and the freezing point of the frozen consumable product;
      the second energy is calculated by multiplying, by the computer, a latent heat of fusion of the frozen consumable product by the quantity; and
      the third energy is calculated by multiplying, by the computer, the non-frozen specific heat value of the frozen consumable product by the measured quantity and by a net temperature difference between a body temperature of the individual and the freezing point of the frozen consumable product;
   calculating, by the computer, a net caloric value of the frozen consumable product, wherein the net caloric value is equal to the gross caloric value of the frozen consumable product less the caloric energy expended by an individual in consuming the frozen consumable product;
   displaying, by the computer in a coherent display, the gross caloric value of the consumable product and the net caloric value of the consumable product; and
   tracking, by the computer, both the gross caloric value and the net caloric value of consumable products consumed by the individual over a predetermined time interval.

5. The method of claim 4, wherein the consumable product comprises water.

6. The method of claim 4, further comprising: comparing, by the computer, the net caloric value over the predetermined time interval to a desired caloric intake over the predetermined interval.

* * * * *